United States Patent
Edler et al.

(10) Patent No.: US 10,744,322 B2
(45) Date of Patent: Aug. 18, 2020

(54) COCHLEAR IMPLANT, DEVICE FOR GENERATING A CONTROL SIGNAL FOR A COCHLEAR IMPLANT, DEVICE FOR GENERATING A COMBINATION SIGNAL AND COMBINATION SIGNAL AND CORRESPONDING METHODS

(75) Inventors: Bernd Edler, Hannover (DE); Andreas Buechner, Isenhagen (DE); Waldo Nogueira, Brussels (BE); Frank Klefenz, Mannheim (DE)

(73) Assignee: FRAUNHOFER-GESELLSCHAFT ZUR FOERDERUNG DER ANGEWANDTEN FORSCHUNG E.V., Munich (DE)

( * ) Notice: Subject to any disclaimer, the term of this patent is extended or adjusted under 35 U.S.C. 154(b) by 1927 days.

(21) Appl. No.: 12/067,222

(22) PCT Filed: Sep. 5, 2006

(86) PCT No.: PCT/EP2006/008650
§ 371 (c)(1),
(2), (4) Date: Sep. 29, 2008

(87) PCT Pub. No.: WO2007/033762
PCT Pub. Date: Mar. 29, 2007

(65) Prior Publication Data
US 2009/0157143 A1   Jun. 18, 2009

(30) Foreign Application Priority Data

Sep. 19, 2005 (DE) .................. 10 2005 044 628
Oct. 13, 2005 (DE) .................. 10 2005 049 507

(51) Int. Cl.
*A61N 1/36* (2006.01)
*H04R 25/00* (2006.01)
*A61N 1/08* (2006.01)

(52) U.S. Cl.
CPC ............ *A61N 1/36036* (2017.08); *A61N 1/08* (2013.01); *H04R 25/606* (2013.01)

(58) Field of Classification Search
CPC .. A61N 1/36032; A61N 1/082; A61N 1/0541; A61N 1/08; H04R 25/606; A61F 11/04
See application file for complete search history.

(56) References Cited

U.S. PATENT DOCUMENTS

| 5,095,904 A | 3/1992 | Seligman et al. |
| 5,271,397 A | 12/1993 | Seligman et al. |

(Continued)

FOREIGN PATENT DOCUMENTS

| DE | 38 30 496 C1 | 9/1996 |
| EP | 1 207 718 A2 | 5/2002 |

(Continued)

OTHER PUBLICATIONS

English translation of the official communication issued in counterpart European Application No. 06 777 168.3, dated Apr. 17, 2009.

(Continued)

*Primary Examiner* — Lindsey G Wehrheim
(74) *Attorney, Agent, or Firm* — Keating & Bennett, LLP

(57) ABSTRACT

A cochlear implant for processing signal parameters which are adapted for controlling the cochlear implant, which are based on the audio signal and which enable generating a representation of the audio signal by the cochlear implant includes a receive interface which is implemented to receive the signal parameters and a nerve stimulator for processing the signal parameters to generate nerve cell stimulation signals based on the signal parameters. A device for generating a control signal for a cochlear implant on the basis of an audio signal includes a cochlear parameter extractor for analyzing the audio signal which is implemented to generate signal parameters as input information for the cochlear (Continued)

implant based on an analysis of the audio signal using a human hearing simulation model, and a transmit interface for transmitting the signal parameters to the cochlear implant.

23 Claims, 9 Drawing Sheets

(56) References Cited

U.S. PATENT DOCUMENTS

| | | | |
|---|---|---|---|
| 5,762,292 | A | 6/1998 | Schweyer et al. |
| 5,950,161 | A | 9/1999 | Kozuma et al. |
| 6,231,604 | B1* | 5/2001 | von Ilberg .................. 623/10 |
| 6,249,704 | B1 | 6/2001 | Maltan et al. |
| 6,728,578 | B1 | 4/2004 | Voelkel |
| 6,732,046 | B1 | 5/2004 | Joshi |
| 2002/0031242 | A1 | 3/2002 | Yasui et al. |
| 2003/0171786 | A1* | 9/2003 | Blamey et al. ............ 607/57 |
| 2005/0033384 | A1* | 2/2005 | Sacha ............ A61N 1/36032 607/57 |
| 2005/0187592 | A1* | 8/2005 | Seligman ........ A61N 1/36032 607/57 |
| 2005/0209657 | A1* | 9/2005 | Chung et al. .............. 607/57 |
| 2006/0149458 | A1 | 7/2006 | Costello et al. |
| 2006/0210116 | A1 | 9/2006 | Azuma |

FOREIGN PATENT DOCUMENTS

| | | |
|---|---|---|
| EP | 1 677 076 A2 | 7/2006 |
| JP | 9-8752 A | 1/1997 |
| JP | 2004-500788 A | 1/2004 |
| JP | 2004-207821 A | 7/2004 |
| WO | 96/12383 A1 | 4/1996 |
| WO | 01/99470 A1 | 12/2001 |

OTHER PUBLICATIONS

Official communication issued in counterpart European Application No. 06 777 168.3, dated Apr. 17, 2009.

Official communication issued in counterpart International Application No. PCT/EP2006/008650, dated Nov. 2, 2006.

"Ace Speech Coding Strategy," Nucleus Technical Reference Manual; Z43470; Issue 3; Cochlear Corporation; Dec. 2002; pp. 3.5-3.15.

Baumgarte: "Ein Psychophysiologisches Gehormodell Zur Nachbildung Von Wahrnehmungsschwellen Fur Die Audiocodierung," Dissertation; University of Hanover, Germany; Feb. 2000; 179 pages.

Heinz et al.: "Using a Physiological Ear Model for Automatic Melody Transcription and Sound Source Recognition," Audio Engineering Society Convention Paper 5807; Mar. 22-25, 2003; pp. 1-12.

Nogueira et al.: "A Psychoacoustic "NofM"—Type Speech Coding Strategy for Cochlear Implants," University of Hanover, Germany; Mar. 10, 2005; pp. 1-26.

Translation of Official Communication issued in corresponding International Application PCT/EP2007/011437, dated Aug. 13, 2009.

Official Communication issued in corresponding Japanese Patent Application No. 2008-531563, dated Nov. 30, 2010.

\* cited by examiner

COCHLEAR IMPLANT, DEVICE FOR GENERATING A CONTROL SIGNAL FOR A COCHLEAR IMPLANT, DEVICE FOR GENERATING A COMBINATION SIGNAL AND COMBINATION SIGNAL AND CORRESPONDING METHODS

TECHNICAL FIELD

The invention generally relates to a cochlear implant, to a device for generating a control signal for a cochlear implant, to a device for generating a combination signal, to a combination signal and to corresponding methods, in particular to a concept for transmitting and storing audio signals for cochlear implants.

BACKGROUND

In the following, first of all the basics regarding the operation of cochlear implants are discussed to improve and/or facilitate an understanding of the present invention. Patients with a complete loss of their hearing sense often receive so-called cochlear implants which enable the generation of sound stimuli by electric impulses in the inner ear. For a better understanding, FIG. 7a shows a schematical illustration of a human ear, wherein the cochlea is illustrated in a rolled-off form. As it may be seen from the schematical illustration 700 of FIG. 7a, a sound stimulus generates an oscillation on a basilar membrane of the cochlea which is converted into neural impulses with the help of hairs and associated auditory cells. In a healthy hearing system, a conversion of audio frequencies into positions along the basilar membrane takes place in the cochlea. In other words, depending on the frequency of an incoming sound, an area of the basilar membrane corresponding to the frequency is excited especially strongly.

FIG. 7b shows a schematical illustration of a human ear into which electrodes of a cochlear implant are introduced. From the graphical illustration 750 of FIG. 7b it may be seen that a cochlear implant comprises several electrodes 760 which are placed at different positions along the basilar membrane in the cochlea. By suitable impulse patterns applied to the electrodes 760, a cochlear implant may thus perform an approximation, even if only coarse, of the stimuli which occur in a healthy hearing system. It is to be noted here that a cochlear implant typically directly excites one auditory nerve and/or several auditory nerves.

A conventional cochlear implant here comprises a microphone for sound reception and a signal processing unit for converting the sound signal into suitable stimulation impulses. The quality of the sounds heard by a patient with a cochlear implant is here limited by several factors. On the one hand, the number of implantable electrodes is limited, so that a frequency resolution of a healthy ear cannot be achieved. Further, the number of impulses which may be generated per time unit is strongly limited by a transmission path to the electrodes. Finally, the efficiency of the signal processing unit is further usually limited by a limitation of the current reception for achieving a sufficient operation time with a predetermined battery capacity.

In the following, a conventional signal processing for the cochlear implant is described. Currently, conventional cochlear implants have up to 22 electrodes which may respectively be activated by electrical impulses (stimulation). The respective impulse strength of an electric impulse determines the strength of the stimulus which is passed on via the auditory nerve to the brain. The position of an electrode here corresponds to the pitch or frequency of a tone, respectively, which would cause a maximum alignment of the basilar membrane of the cochlea in a healthy hearing system at the corresponding location, i.e. at the position of the electrode. Thus, conventionally, in the signal processing unit the incoming sound signal is split up by bandpass filters into the corresponding frequency portions, wherein for this purpose, for example, a filter bank is needed. The needed impulse strength for electrodes at different positions may then be derived from a signal strength in the associated frequency bands.

As conventionally at a time only one electrode may be stimulated, the control takes place sequentially, for example in a multiplex. Here, the sequence of the controlled electrodes may vary. If all electrodes were controlled in succession, due to the limitation of the overall stimulation rate for each individual electrode a time resolution would result which is too low. Thus, a method was developed which, in a certain time section, selects a lower number of electrodes according to the corresponding signal strength. If the stimulation in a cycle is limited to N selected electrodes with an overall number of M electrodes, this is a so-called NofM strategy, which is also referred to as an advanced combinational encoder (ACE). A detailed description of the advanced combinational encoder may, for example, be found in the technical reference manual "ACE Speech Coding Strategy" (Nucleus Technical Reference Manual, Z43470 Issue 3, Cochlear Corporation, December 2002). The overall stimulation cycle is thus shortened from M impulses to N impulses, which leads to an increase of time resolution. Conventional numerical values here are M=22 and N=8.

The NofM strategy comprises the problem that the frequency ranges with the highest signal strengths are not the most important ones for perception. Thus, by the Laboratory for Information Technology of the University of Hanover (Germany) in cooperation with the Auditory Center Hanover (Germany) approaches for improvement were developed which use psychoacoustic models for selecting the electrodes, as they are also used in audio encoding. For this new method, also referred to as psychoacoustic advanced combinational encoder (PACE) the computing power of existing signal processing units is still sufficient. Examinations with patients have further indicated that the mentioned approach may increase speech intelligibility.

FIG. 8 shows a schematical illustration of conventional devices for coupling audio signals into a cochlear implant. The schematical illustration of FIG. 8 is designated by 800 in its entirety. The schematical illustration 800 describes a transmission path of audio signals from an audio signal origin to a cochlear implant. With today's conventional digital transmission of audio signals it is normal to encode an audio signal 810 in an encoder 820. The encoder may, for example, be part of a (broadcast) transmitter and be realized in hardware or in software. An encoded audio signal 822 is transmitted via a broadcasting link in a radio transmission and then received by a receiver 830. In the receiver, typically a frequency conversion and further a decoding takes place. The receiver may, for example, be a broadcasting receiver or a television receiver. For radio or television reception an acoustic transmission from the broadcast (radio or television) receiver 830 to a signal processing unit 850 of the cochlear implant 834 is a simple and advantageous possibility. In this case, the audio signal is reproduced by the broadcast receiver 830 via a loudspeaker 840. The cochlear implant includes in the mentioned case a microphone 844 which receives the decoded audio signal reproduced by the loudspeaker 840 and passes the same on to the signal processing unit 850 located in the cochlear implant. The signal processing unit 850 thereupon generates stimulation impulses for the excitation of auditory nerves based on the audio signal provided by the microphone 844. The stimulation impulses may then be supplied to electrodes which excite the auditory nerves of a human patient.

It is further sometimes advantageous to directly transmit a decoded audio signal provided by the decoding to the cochlear implant 834. For such a direct transmission, for example induction loops 860, 862 may be used, whereby the transmission is insensitive towards interfering noise. If instead of a broadcast receiver a mobile player is used, like, for example, a portable CD player or an MP3 player, then usually the audio signal and/or sound signal of the signal processing unit 850 of the cochlear implant 834 may also be directly supplied via a cable.

In summary it may be noted, that the cochlear implant 834 conventionally receives an audio signal which was decoded by a broadcast receiver or a media player. It has been shown, however, that the conventional concept does not guarantee an optimal speech quality.

SUMMARY

According to an embodiment, a cochlear implant for processing signal parameters which are based on an audio signal which are adapted for controlling the cochlear implant and which enable generating a representation of the audio signal by the cochlear implant may have a receive interface which is implemented to receive the signal parameters and a nerve stimulator for processing the signal parameters to generate nerve cell stimulation signals based on the signal parameters.

According to an embodiment, a device for generating a control signal for a cochlear implant on the basis of an audio signal may have a cochlear parameter extractor for analyzing the audio signal which is implemented to generate signal parameters as input information for the cochlear implant based on an analysis of the audio signal using a human hearing simulation model and a transmit interface for transmitting the signal parameters to the cochlear implant, wherein the device is implemented to be arranged outside an ear into which the cochlear implant is introduced.

According to an embodiment, a device for generating a combination signal based on an audio signal may have a provider for providing signal parameters depending on the audio signal which are adapted for controlling a cochlear implant and which are implemented to generate a representation of the audio signal by the cochlear implant, and a signal combiner for combining the audio signal and the signal parameters, wherein the combination signal is obtained.

According to an embodiment, a combination signal may have an audio signal and signal parameters which are adapted for controlling a cochlear implant and which are implemented to generate a representation of the audio signal by the cochlear implant.

According to an embodiment, a method for operating a cochlear implant may have the steps of receiving signal parameters which are adapted for controlling the cochlear implant, which represent an audio signal and which enable generating a representation of the audio signal by the cochlear implant, and processing the signal parameters to generate nerve cell stimulation signals based on the signal parameters.

According to an embodiment, a method for generating a combination signal based on the audio signal may have the steps of providing signal parameters depending on the audio signal which are adapted for controlling a cochlear implant, which are based on the audio signal and which enable generating a representation of the audio signal by the cochlear implant, and combining the audio signal and the signal parameters to obtain the combination signal.

According to an embodiment, a method for generating a control signal for a cochlear implant on the basis of an audio signal in a device which is implemented to be arranged outside an ear into which the cochlear implant is introduced may have the steps of analyzing an audio signal using a human hearing simulation model to obtain signal parameters as input information for the cochlear implant, and transmitting the signal parameters to the cochlear implant.

According to an embodiment, a computer program may have a program code for performing, when the computer program runs on a computer, a method for generating a combination signal based on the audio signal, wherein the method may have the steps of providing signal parameters depending on the audio signal which are adapted for controlling a cochlear implant, which are based on the audio signal and which enable generating a representation of the audio signal by the cochlear implant; and combining the audio signal and the signal parameters to obtain the combination signal.

The present invention provides a cochlear implant for processing signal parameters which are adapted for controlling (or activating or triggering) the cochlear implant, which are based on an audio signal and/or represent an audio signal, and which enable the generation of a representation of the audio signal by the cochlear implant. An inventive cochlear implant includes a receive interface which is implemented to receive the signal parameters and a nerve stimulation means for processing the signal parameters to generate the nerve cell stimulation signals based on the signal parameters.

The present invention is based on the finding that it is advantageous if a cochlear implant comprises a receive interface which is implemented to receive signal parameters which describe an audio signal to be represented by the cochlear implant. According to the central idea of the present invention, a cochlear implant may typically process signal parameters which describe an audio signal and which are adapted for controlling the cochlear implant substantially more efficiently than the audio signal itself. A cochlear implant cannot itself pass on the audio signal to the human auditory nerves, but it excites the auditory nerves by nerve cell stimulation signals which may be derived from the adapted signal parameters based on a comparatively simple processing.

The inventive use of signal parameters which are based on the audio signal instead of the audio signal itself as an input signal for a cochlear implant enables substantial improvements or simplifications, respectively, in the use of a cochlear implant. As the signal parameters received by the cochlear implant have to be adapted for controlling the cochlear implant, the cochlear implant has to use a substantially lower computing effort for generating the nerve cell stimulation signals based on the signal parameters as would be needed in a generation of the nerve cell stimulation signals based on the audio signal itself. A lower computing effort in the cochlear implant again results in a lower current consumption of the cochlear implant, so that with a constant capacity of a battery a substantially longer operation time of the cochlear implant may be guaranteed.

On the other hand, the energy used in the calculation of the nerve cell stimulation signals may also be used to enable an improved controlling of electrodes which are coupled to nerve cells of the human auditory nerve with a constant operation time.

Further, by receiving signal parameters adapted for controlling the cochlear implant by the cochlear implant it is possible to perform a calculation of the signal parameters outside the cochlear implant. By this, the signal parameters may be determined using a complex calculation instruction so that a speech intelligibility may be achieved which is improved compared to conventional cochlear implants.

Further, the complete hardware overhead is reduced compared to conventional systems, as the signal parameters may be calculated centrally for a plurality of patients with cochlear implants. According to the invention, each individual cochlear implant, however, only has to comprise one receive interface which is implemented to receive the adapted signal parameter and one nerve stimulation means for deriving nerve cell stimulation signals from the signal parameters. A complex signal processing means which is conventionally contained in a cochlear implant to process the audio signal per se may be omitted, however. Thus, cheaper cochlear implants may be realized which still enable the maximum possible speech intelligibility.

Apart from that it is to be noted that an inventive implementation of cochlear implants having a receive interface for signal parameters enables a standardization so that cochlear implants from different manufacturers may operate with the same hearing-adapted signal parameters.

The present invention further provides a device for generating a control signal for a cochlear implant on the basis of an audio signal. An inventive device for generating a control signal for a cochlear implant includes a cochlear parameter extractor for analyzing the audio signal which is implemented to generate, based on an analysis of the audio signal using a human hearing stimulation model, signal parameters as input information for the cochlear implant. An inventive device further includes a transmit interface for transmitting the signal parameters to the cochlear implant. Further, the inventive device is implemented to be arranged outside the ear into which the cochlear implant is introduced.

It is the main idea of the inventive device for generating a control signal for a cochlear implant to calculate signal parameters as input information for the cochlear implant by an external device which is not introduced into the human body and/or is implemented for operation outside the human body. At the inventive device, thus a transmit interface for transmitting the signal parameters to the cochlear implant is further provided.

The signal parameters extracted by the device for generating a control signal for a cochlear implant may be used for controlling more than one cochlear implant. Further, it is possible by an arrangement of the device for generating a control signal for a cochlear implant outside the body to provide an especially high computing power so that input information for the cochlear implant may be processed using a human hearing simulation model. By the use of such a simulation model which, for example, describes a mechanical oscillation excitation of the cochlea by a movement of the basilar membrane, a stimulation of auditory nerves may be achieved by the cochlear implant which enables an especially realistic auditory impression with good speech intelligibility.

The present invention further provides a device for generating a combination signal based on an audio signal having a means for providing signal parameters depending on the audio signal which are suitable for controlling the cochlear implant and/or which are adapted to generate a representation of the audio signal by the cochlear implant, and a signal combiner for combining the audio signal and the signal parameters, whereby the combination signal is obtained.

It has been shown that the formation of a combination signal which includes both the audio signal and also the signal parameters which are adapted for controlling the cochlear implant enables making an audio signal available for an especially great number of persons. The combination signal formed by the inventive device may be reproduced with little effort both for persons with unimpaired hearing and for those with a cochlear implant. The generation of the combination signal with the help of the signal combiner makes it possible for a cochlear implant to use both signal portions, if applicable, i.e. both the audio signal itself and the signal parameters depending on the audio signal. In this case, the cochlear implant, for example, only has to calculate those pieces of information for determining the nerve cell stimulation signals from the audio signal itself which have not been described with sufficient precision by the signal parameters. Thus, the inventive device for generating the combination signal enables developing cochlear implants with reduced effort with regard to signal processing.

Further, the inventive device for generating the combination signal enables the provision of signals both for conventional cochlear implants processing the audio signal per se and also for inventive cochlear implants whose receive interface is implemented to receive the signal parameters. Here, the cochlear implant may, for example, be implemented to extract the signal parameters from the combination signal. The generation of a combination signal thus enables the best possible compatibility of the inventive concept with conventional means.

It is further to be noted that the combination signal is suitable for an especially efficient transmission, for example by a broadcasting station.

The present invention further provides a combination signal having an audio signal and signal parameters which are suitable for controlling a cochlear implant and/or which are adapted to generate a representation of the audio signal by the cochlear implant.

The present invention further provides corresponding methods and computer programs analog to the above-described devices. The methods and computer programs offer the same advantages as the described devices.

BRIEF DESCRIPTION OF THE DRAWINGS

In the following, embodiments of the present invention are explained in more detail with reference to the accompanying drawings, in which.

DETAILED DESCRIPTION

In the following, with reference to FIGS. 1a, 1b and 2 devices are described which may be used as components to realize the inventive concept to supply signal parameters instead of an audio signal to a cochlear implant which are adapted for triggering (or activating or controlling) the cochlear implant.

Figure 1A:
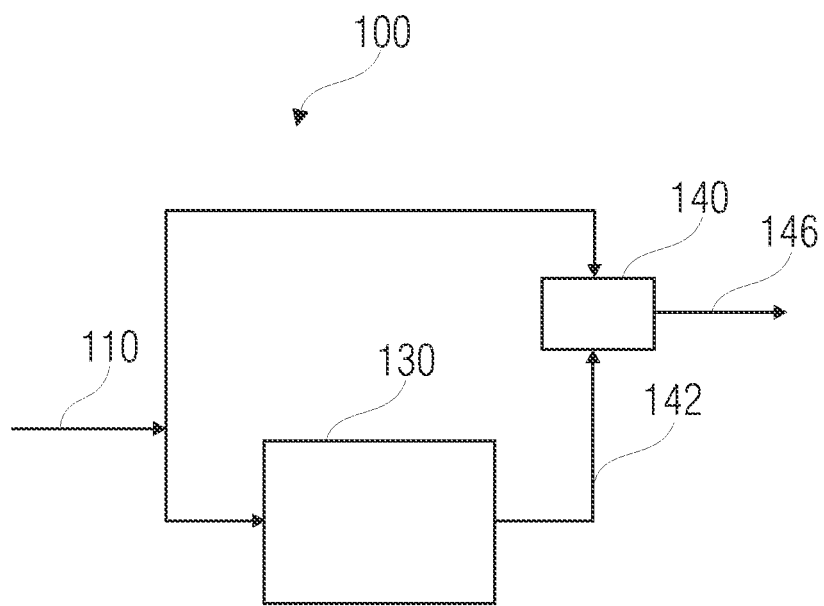
FIG. 1a shows a block diagram of an inventive device for generating a combination signal based on an audio signal according to a first embodiment of the present invention.

FIG. 1a shows a block diagram of an inventive device for generating a combination signal according to a first embodiment of the present invention. The device shown in FIG. 1a is designated by 100 in its entirety. The inventive device 100 is implemented to receive an audio signal 110. The inventive device 100 further includes a means 130 for providing signal parameters 142 depending on the audio signal which are adapted for controlling a cochlear implant and which enable generating a representation of an audio signal by the cochlear implant in a way which necessitates little computing overhead.

The inventive device 100 further includes a signal combiner 140 for combining the audio signal 110 and the signal parameters 142 provided by the means 130 for providing signal parameters. The signal combiner 140 thus provides a combination signal 146 in which the audio signal 110 and the signal parameters 142 are combined.

Figure 1B:
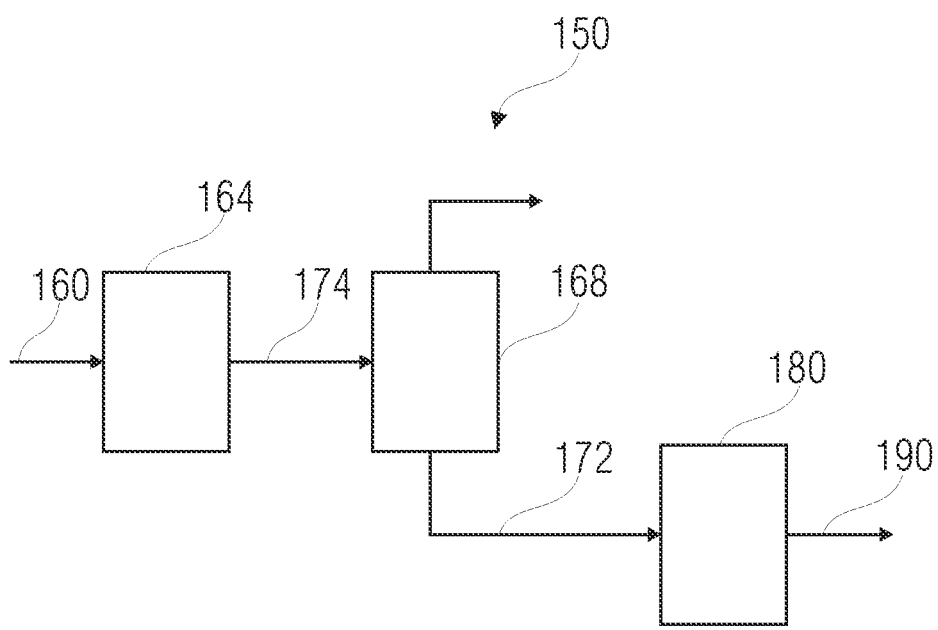
FIG. 1b shows a block diagram of an inventive receiver for providing signal parameters based on a combination signal according to a second embodiment of the present invention.

FIG. 1b further shows a block diagram of an inventive means for providing signal parameters based on a combination signal. The device of FIG. 1b is designated by 150 in its entirety. The device 150 is implemented to receive a receive signal and/or a combination signal 160 which includes at least one audio signal and signal parameters depending on the audio signal which are adapted for controlling a cochlear implant. The device 150 optionally includes a channel selection means 164 which is implemented to select a channel from the received signal 160 which includes a combination signal consisting of an audio signal and associated signal parameters. In other words, the channel selection means 164 is implemented to pass on a channel from a plurality of channels contained in the received signal 160 to a signal parameter extractor 168. The signal parameter extractor 168 is implemented to extract signal parameters 172 from the combination signal 174 supplied to the same which are contained in the receive signal 160. The signal parameter extractor 168 may include a data separation means which is implemented to extract a partial data stream 172 from a received data stream 174 (which includes a combination signal). The inventive device 150 further includes a signal parameter transmit means 180 which is implemented to receive the signal parameters 172 and generate a signal parameter transmit signal 190 based thereupon. Here, the signal parameter transmit means may apply a channel encoding and/or a source encoding to the signal parameters 172. The signal parameter transmit means may further be implemented to generate the signal parameter transmit signal 190 such that the signal parameter transmit signal 190 is suitable for a wireless transmission. The signal parameter transmit signal 190 may, for example, be generated such that it is suitable for controlling an induction loop, with the help of which a coupling to a cochlear implant may be produced. The signal parameter transmit signal may further, however, also be implemented for a wireless broadcasting with the help of an electromagnetic far-field coupling. The signal parameter transmit means 180 may for this purpose include a means for converting to a carrier frequency and a modulation means. It is noted, however, that the signal parameter transmit signal 190 may also be implemented for a wire-bonded transmission of the signal parameter 172.

Figure 2:
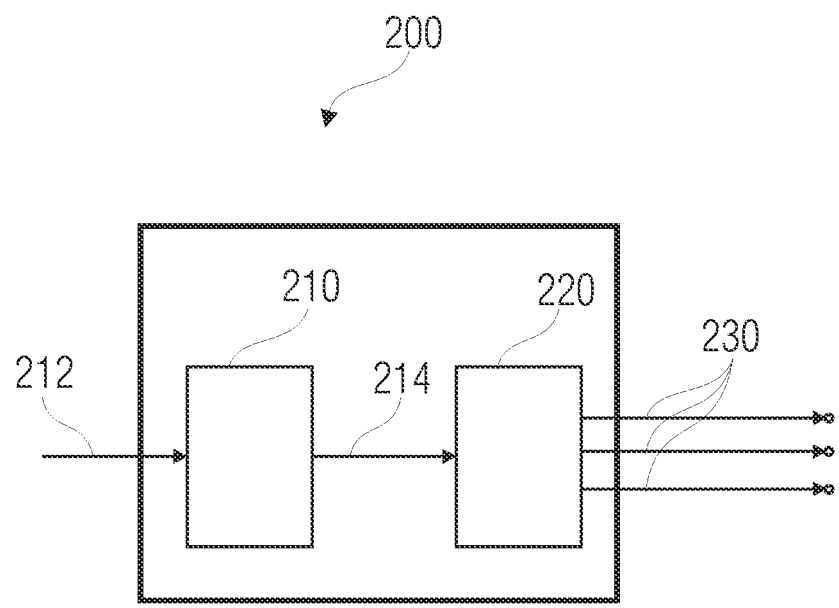
FIG. 2 shows a block diagram of an inventive cochlear implant according to a third embodiment of the present invention.

FIG. 2 shows a block diagram of an inventive cochlear implant according to a third embodiment of the present invention. The cochlear implant illustrated in FIG. 2 is designated by 200 in its entirety. The cochlear implant 200 includes a receive interface 210 which is implemented to receive signal parameters which are adapted for controlling the cochlear implant, which are based on an audio signal and which enable generating a representation of the audio signal by the cochlear implant. The receive interface 210 is implemented to receive a signal parameter receive signal 212 and to derive signal parameters 214 based thereupon. The receive interface 210 is here implemented for coupling to a receive induction loop or an antenna to wirelessly receive the signal parameter receive signal 212. Alternatively, the receive interface 210 may also include a line receiver, however, to receive a signal parameter receive signal 212 transmitted in a wire-bonded manner. The receive interface 210 may further optionally include a means for frequency conversion, a demodulator, a channel decoder and/or a source decoder which are implemented to derive the signal parameters 214 from the signal parameter receive signal 212.

Further, the receive interface 210 may include a selection means to pass on only one part of the information contained in the signal parameter receive signal 212 as signal parameters 214. The selection means may here be implemented to process only one channel of several channels contained in the signal parameter receive signal 212. Further, the selection means may be implemented to separate the signal parameters from an audio signal portion which may additionally be contained in the signal parameter receive signal 212 to thus enable that only the signal parameters are provided at the output of the receive interface 210.

The cochlear implant 200 further includes a nerve stimulation means 220 which is implemented to receive and process the signal parameters 214 to provide nerve cell stimulation signals 230 based on the signal parameters 214. The nerve stimulation means is implemented such that the nerve cell stimulation signals 230 are adapted to excite electrodes of the cochlear implant 200 for the stimulation of auditory nerves of the human carrier of the cochlear implant 200. The nerve cell stimulation signals 230 are calculated by the nerve stimulation means 220 such that a human carrier of the cochlear implant 200 gains an auditory impression of the auditory signal on which the signal parameters 214 are based due to the excitation of his or her auditory nerves by the nerve cell stimulation signals 230.

Figure 3A:
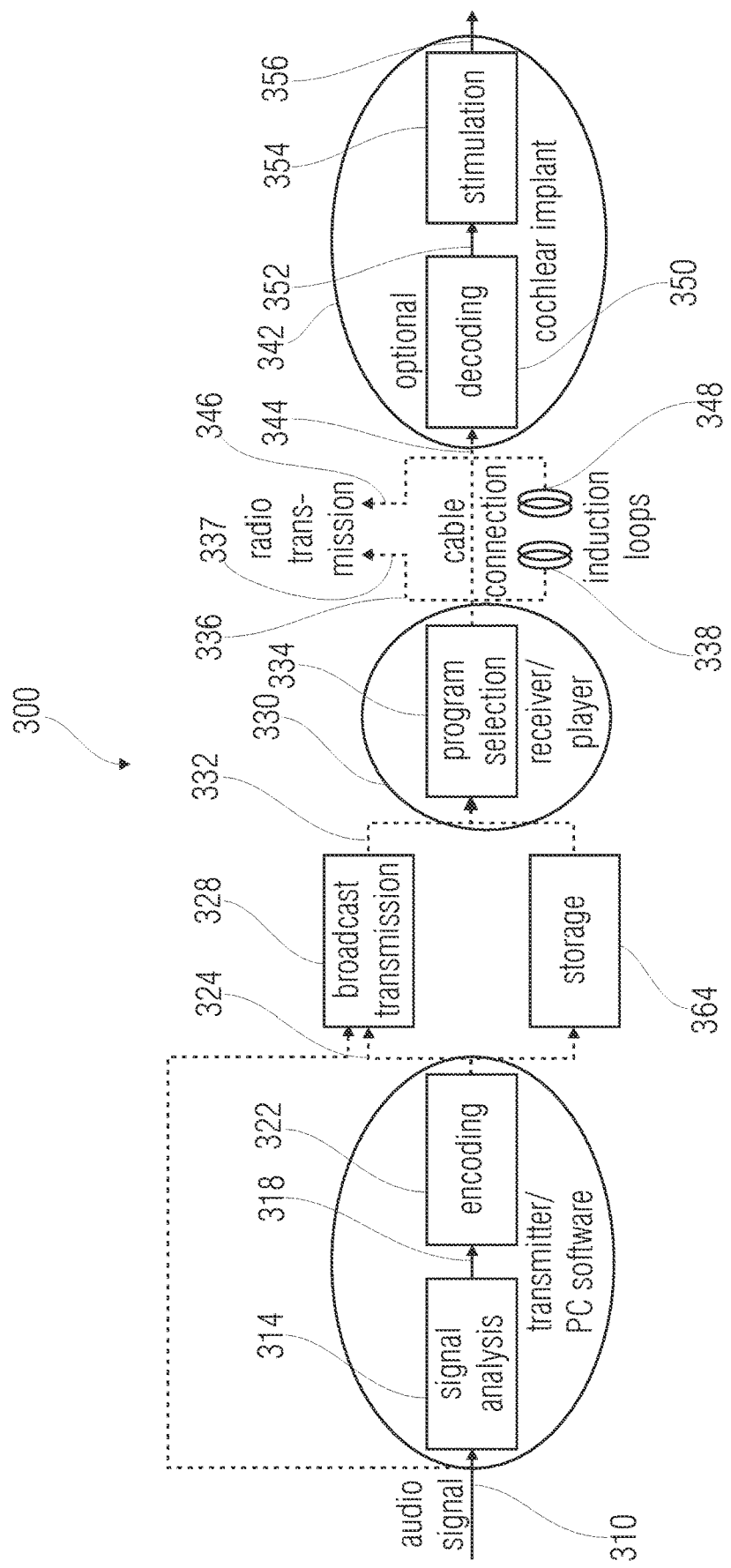
FIG. 3a shows a schematical illustration of an inventive transmission chain to a cochlear implant in a signal analysis before a broadcast transmission or storage according to a fourth embodiment of the present invention.

FIG. 3a shows a schematical illustration of an inventive transmission chain to a cochlear implant in a signal analysis before a broadcast transmission or storage of the audio signal according to a fourth embodiment of the present invention. The schematical illustration of FIG. 3a is designated by 300 in its entirety.

The transmission chain 300 receives an audio signal 310 as input information. Here, it is first assumed that a broadcast transmission of the radio signal 310 takes place. In order to guarantee a most efficient transmission of the audio signal and, simultaneously, particularly good speech intelligibility for a wearer of the cochlear implant, the audio signal 210 is provided to a signal analysis 314 already before broadcast transmission. In the signal analysis 314 signal parameters 318 of the audio signal 310 may be extracted which are adapted for controlling a cochlear implant. In the illustrated embodiment, the signal analysis 314 extracts signal parameters 318 which describe at least one magnitude occurring within or at an output of a human hearing simulation model. In other words, within the scope of the signal analysis 314 the audio signal 310 is supplied to a human hearing simulation model as an input signal and the signal parameters 318 are selected to describe a (relevant) physical magnitude occurring in the hearing model. Further details regarding a possible auditory model used are explained in more detail below with reference to FIG. 3b.

The signal parameters resulting in the signal analysis 314 are then supplied to an optional encoding 322. The encoding 322 may, for example, include a source encoding and/or a channel encoding as they are known from telecommunications. When using the encoding 322 thus encoded signal parameters 324 result which are available for a broadcast transmission 328.

According to the inventive approach, thus for an improvement of speech intelligibility and/or the perceived sound quality of broadcast transmissions for wearers of cochlear implants, a transmitter-side signal processing is used. Here, use is made of the fact that in a broadcast transmission on the transmitter side a high processing power may be provided. By the signal analysis 314, thus signal parameters 318 result which may be taken as preprocessed data. The obtained preprocessed data 318 may thus be suitably encoded within the scope of the encoding 322 in order to obtain encoded signal parameters 324, and the encoded signal parameters 324 may then be transmitted within the scope of the broadcast transmission 328 together with the broadcast signal as side information. The broadcast signal transmitted within the scope of the broadcast transmission 328 here includes the audio signal 310 and the encoded signal parameters 324.

It is to be noted, that in particular with digitally transmitted broadcast programs adding one or several pieces of side information to the actual sound and/or image signals is easily possible. It is further to be noted that within the scope of the broadcast transmission 328 thus a combination signal consisting of the audio signal 310 and signal parameters 318 extracted therefrom may be transmitted, wherein the generation of the combination signal 146 based on the audio signal 110 was already illustrated with reference to FIG. 1a.

The broadcast transmission 328 may, besides, further include a frequency conversion, a modulation and/or channel encoding for increasing the reliability of transmission.

It is further to be noted, that the encoded signal parameters 324 may be combined with the (optionally encoded) audio signal 310 in different ways. Within the scope of a digital signal transmission, for example a first group of bits may be associated with the encoded audio signal 310 within a bit frame, while a second group of bits is associated with the encoded signal parameters 324 within the bit frame. An association may here be given statically or also dynamically depending on the amount of data arising of the encoded audio signal and the encoded signal parameters 324. Further, it is possible to associate a first group of sub-carriers to the (possibly encoded) audio signal 310 in the broadcast transmission 328 and further associate a second group of sub-carriers to the encoded signal parameters 322, wherein the sub-carriers of the first group of sub-carriers and the sub-carriers of the second group of sub-carriers belong to the same main carrier. In a further embodiment it is possible to emit the (possibly encoded) audio signal 310 and the encoded signal parameters 324 with different carrier frequencies.

It is further noted here that for a transmission of the (possibly encoded) audio signal 310 and the encoded signal parameters 324 also any other transmission method is suitable which enables separating the encoded audio signal 310 and the encoded signal parameters 324 again on the receive side.

In summary, it may be said that an inventive transmitter-side signal processing basically fulfils the following tasks:
analysis 314 of an audio signal 310 and/or a sound signal using a software human hearing simulation model,
extraction of parameters (also designated as signal parameters 318) which are suitable for an efficient controlling of a cochlear implant, and
encoding 322 the parameters 318 for an efficient transmission of the parameters 318 as side information.

In case of a broadcast transmission, the inventive transmission chain 300 further includes a receiver 330. The receiver 330 receives a broadcast transmission signal 332 transmitted within the scope of the broadcast transmission 328 and is further implemented to select transmitted information to be received with the help of a program selection means based on the broadcast transmission signal 322. The program selection means 334 may here select a predetermined channel from a plurality of broadcast transmission signals 332 received by a receiver 330 by transmitting the audio signal 310 to be received (encoded if applicable) together with the encoded signal parameters 324. The program selection means 334 may achieve the corresponding selection by filtering out a certain frequency range and/or by selecting certain time slots and/or by a selection of signal portions in the broadcast transmission signal 332 which are encoded with a certain code. The program selection means 334 is implemented to provide a signal 336 at its output which includes the encoded signal parameters 324. The signal 336 at the output of the program selection means 334 may further optionally also include the encoded audio signal 310 (for example in the form of a combination signal). The receiver 330 further includes a signal transmission means which is not illustrated here which is implemented to process the signal 366 for a transmission to a cochlear implant 342. For example, the receiver 330 may be implemented to enable a broadcast transmission of the signal 336 provided by the program selection means 334 to the cochlear implant 342 by the receiver 330 providing a transmit signal for controlling an antenna 337. Likewise, the receiver 330 may be implemented to feed an induction loop 338 which is deposited to enable a transmission of the signal 336 to the cochlear implant 342. The receiver 330 may further alternatively include a line driver which enables a transmission of the signal 336 with the encoded signal parameters 324 via a wire-bonded connection to the cochlear implant 342.

In the illustrated embodiment, the cochlear implant 342 is implemented to receive an implant receive signal 344 which is based on the signal 336 provided by the receiver 330 at the output of the program selection means 344. For this purpose, the cochlear implant 342 may, for example, comprise a receive antenna 346 to receive the implant receive signal 344 which contains the encoded signal parameters 324. The cochlear implant 342 may additionally or alternatively include an implant induction loop 348 to receive the implant receive signal 344. Further, the cochlear implant may optionally comprise a line receiver which is implemented to receive the signal 336 as an implant receive signal 344 via a cable connection from the program selection means 334 of the receiver 330.

The cochlear implant 342 is implemented to decode the implant receive signal 344 in a decoder 350 to obtain decoded signal parameters 352. The cochlear implant 342 is implemented such that the decoded signal parameters 352 correspond to the signal parameters 318 resulting in the transmitter-side signal analysis 314. The cochlear implant 342 and/or the associated decoder 350 may, however, optionally be implemented so that only a real subset of the signal parameters 318 provided on the transmitter-side are provided as decoded signal parameters 352.

Further, the cochlear implant 342 is implemented to generate, based on the decoded signal parameters 352, nerve cell stimulation signals and/or nerve cell stimulation impulses 356, which are implemented to excite nerve cells of a human (or animal) auditory nerve via suitable electrodes.

In summary, it may thus be noted that a signal processing means of an inventive cochlear implant 342 only has to perform the following two steps:

decoding 350 the side information (added to the broadcast transmission signal 332 in the broadcast transmission 328), and
   converting 354 the received parameters 352 into stimulation impulses 356.

It is to be noted, that the functionality of the cochlear implant 342 may in general also correspond to the functionality of the cochlear implant 200 described with reference to FIG. 4. The decoder 350 is here to be regarded as optional, if a decoding of the encoded signal parameters 324 already takes place within the receiver 330. In this case, thus non-encoded signal parameters may directly be transmitted wirelessly or by wire bonding to the cochlear implant 342. It is further to be noted, that the cochlear implant 342 may be implemented to separate a side signal occurring within the scope of the broadcast transmission 328 which contains the encoded signal parameters 324 from a main signal occurring in the broadcast transmission 328 which contains the encoded audio signal 310. In this case, the corresponding functionality may be omitted in the receiver 330.

Apart from that, an inventive cochlear implant 342 may further optionally also comprise a program selection means whose functionality corresponds to the functionality of the program selection means 334. Thus, the cochlear implant 342 may optionally directly receive the broadcast transmission signal 332 occurring in the broadcast transmission 328. It is only decisive here that the cochlear implant 342 is implemented to receive a signal which contains (possibly encoded) signal parameters 324 which are adapted for controlling the cochlear implant, and which occur as internal state variables or output variables of a human hearing simulation model.

It is further to be noted that a storage 364 of the encoded signal parameters 324 on a storage medium may take the place of the broadcast transmission 328. A storage medium may, for example, be a semiconductor memory or an optical or magnetic storage medium, like, for example, an RAM memory, an ROM memory, a PROM memory, an EPROM memory, an EEPROM memory, a FLASH memory, a CDROM, a DVD, a magnetic band or any other memory means suitable for a volatile or non-volatile storage of information. Here a player takes the position of the receiver 330 which is implemented to read out information deposited in the used memory medium during storage 364, wherein this information includes encoded signal parameters 324, and pass on a signal 336 which includes the encoded signal parameters 324 to the cochlear implant 342 in the above-described way. The player may here be implemented to select predetermined information from the storage medium used during storage 364.

It is to be noted here that during storage 364 for example only the encoded signal parameters 324 may be stored as useful information. On the other hand, it is possible, however, that the storage medium also includes the audio signal 310 in an encoded form apart from the encoded signal parameters. In this case, the same storage medium may be used both for a reproduction of the audio signal per se and also for a reproduction of the signal parameters 324 belonging to the audio signal. Either the corresponding reproduction means (player) or the cochlear implant 342 may here be implemented to extract the encoded signal parameters 324 from the combined data contained on the storage medium.

It may thus be noted, that an audio signal 310 and/or a sound signal may be rendered in the same way for storage and/or reproduction in mobile players specially adapted for wearers of cochlear implants, as was already described for a broadcast transmission. Here the storage 364 on the corresponding medium takes the place of a transmission as side information, wherein the medium may, for example, be a memory card or a data CD. The reproduction means also referred to as player only needs to provide the encoded data which, for example, describe and/or represent the encoded signal parameters 324 to the signal processing unit of the cochlear implant. The signal processing unit of the cochlear implant 342 then takes over the further processing, as described above, to generate nerve cell stimulation signals 356.

As a connection from the receiver 330 and/or from the reproduction means (player) to the cochlear implant 342 a cable connection or an inductive transmission of the digital control data (i.e. the encoded signal parameters 324) may be used. By an extension of the receiver 330 and/or the reproduction means by a corresponding transmit unit and of the cochlear implant 342 by a corresponding receive unit, also a radio link may be used for the transmission of the encoded signal parameters 324.

In the following, it is described in detail how the signal parameters 318 may be generated, as the use of suitable signal parameters which are adapted for controlling the cochlear implant 342 has a substantial influence on how strongly speech intelligibility may be improved by the inventive concept. It has been found that an improvement of a perceived sound quality for patients with already implanted cochlear implants may only be achieved by an improvement of signal processing when generating nerve cell stimulation signals based on the underlying audio signal. It has been shown here, that a computer simulation model may model the stimuli of the nerve cells of a healthy hearing system so that the strength and sequence of the simulation impulses and/or nerve cell simulation signals may be selected such that the cochlear implant will generate stimuli as similar as possible to those expected on the basis of the computer simulation model for the auditory nerves of an isolated hearing system. It has also been shown, however, that a suitable simulation model necessitates such a high computing overhead that currently an integration of the simulation model into the signal processing means of a cochlear implant is not possible.

In other words, a substantial possibility of improvement compared to conventional cochlear implants is to use a software human hearing simulation model when generating nerve cell stimulation signals 356. Here, it is advantageous that the software simulation model is strongly orientated to the physiology of the ear, whereby the software simulation model is able to model oscillation processes with a high accuracy which an audio signal 310 and/or a sound signal generates in an unimpaired hearing system. An exemplary, suitable software simulation model is described in the dissertation "Ein psychophysiologisches Gehörmodell zur Nachbildung von Wahrnehmungsschwellen für die Audiocodierung" by F. Baumgarte (Diessertation, University of Hanover, Germany, February 2000). An extension of the mentioned software simulation model by a model for converting oscillations into nerve signals even allows simulating neural activities of an auditory nerve. For details in this respect, reference is made to the conference contribution "Using a physiological ear model for automatic melody transcription and sound source recognition" by T. Heinz and A. Brückmann (AES Convention, March 2003, Amsterdam).

For the selection and controlling of the electrodes of the cochlear implant 342 such a simulation model may be very helpful, as it enables a strategy in the selection and controlling of the electrodes which models neural activities of a healthy hearing system as accurately as possible by electric stimulation. Such a simulation model, which may, besides, be implemented in software or hardware, necessitates such a high computing overhead, however, that a computing performance of conventional signal processing units (in cochlear implants) is not sufficient for this purpose.

Figure 3B:
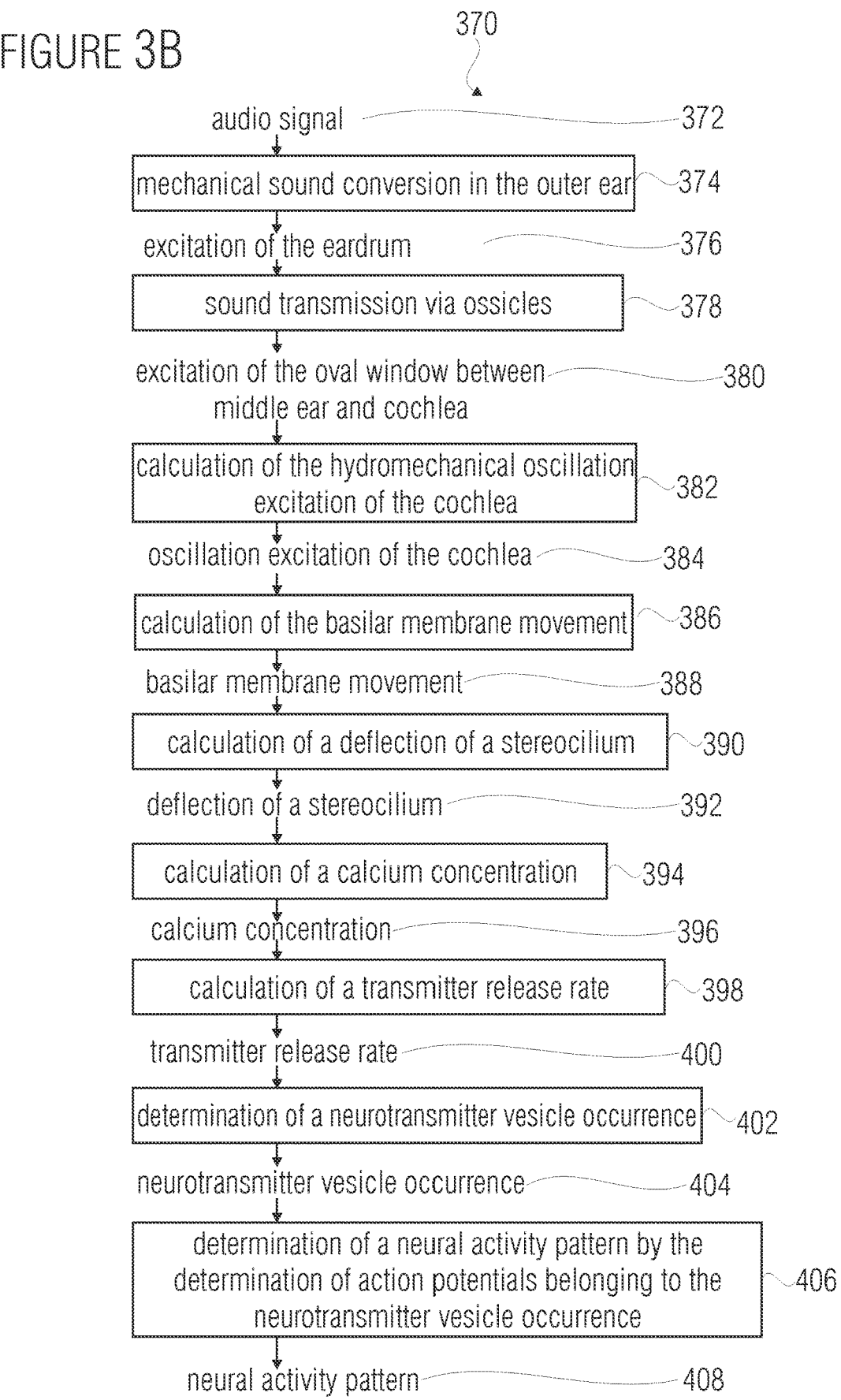
FIG. 3b shows a schematical illustration of a process flow in a simulation of human hearing and of the intermediate and final results occurring in the simulation.

In the following, with reference to FIG. 3b an exemplary simulation model is described in more detail. FIG. 3b shows a schematical illustration of a process flow in a human hearing simulation and of intermediate and final results occurring in the simulation. The graphical illustration of FIG. 3b is designated by 370 in its entirety. An audio signal 372 serves as an input signal for the simulation model 370. Based on the audio signal 372, in a first step 374 a mechanical sound conversion in an outer ear may be evaluated, whereby an excitation 376 of an eardrum may be determined. In a second step 378 a sound transmission via ossicles is calculated, whereby from the excitation 376 of the eardrum an excitation 380 of an oval window between a middle ear and a cochlea may be calculated. In a third step 382, a hydromechanical oscillation excitation 384 of the cochlea is calculated. In a fourth step 386, from the oscillation excitation 384 of the cochlea a basilar membrane movement 388 may be determined. In a fifth step 390, a deflection 392 of a stereocilium is concluded from the basilar membrane movement 388. Based on the deflection 392 of the stereocilium, then in a sixth step 394 a calcium concentration 396 in a hair cell may be calculated. The calcium concentration 396 is then used to calculate a transmitter release rate 400 of transmitter substances in a seventh step 398. Based on the transmitter release rate 400, in an eighth step 402 a neurotransmitter vesicle occurrence 404 is derived which describes an occurrence of neurotransmitter vesicles. Finally, in a ninth step 406 a neural activity pattern 408 may be derived from the neurotransmitter vesicle occurrence 404. The neural activity pattern 408 here approximately describes an activity on nerve cells of a (human or animal) auditory nerve occurring in a healthy hearing system. The neural activity pattern 408 is thus very suitable for providing information on the best possible stimulation of auditory nerves by a cochlear implant 342.

It is to be noted here, that in the simulation model 370 several of the steps 374, 378, 382, 386, 390, 394, 398, 402, 406 may be combined without calculating a corresponding intermediate result. In other words, several steps may be processed in a simplified step without a calculation of the intermediate step illustrated in the graphical illustration 370.

It is further to be noted that as signal parameters for an application of the inventive concept such intermediate results of the process flow illustrated in the schematical illustration 370 are used, whose calculation necessitates, based on the audio signal, at least 50% of the overall computing overhead necessary for the computation of the nerve cell stimulation signals 356 based on the audio signal. In other words, the signal parameters are selected such that the calculation of the nerve cell stimulation signals based on the signal parameters necessitates a lower computing overhead than a calculation of the signal parameters based on the audio signal.

It has further been shown, that it is advantageous when the internal state variables used as signal parameters may be used by a plurality of different cochlear implants with different arrangements of the electrodes and/or different stimulation mechanisms in the calculation of the nerve cell stimulation signals 356 from the audio signal 310.

In this regard it has been shown that the oscillation excitation 384 of the cochlea, which describes the excitation of the fluid contained in the cochlea via the oval window between the middle ear and the cochlea, may advantageously be described by signal parameters. In other words, the signal parameters 318 may be selected to describe the oscillation excitation of the cochlea.

It is further similarly advantageous when the signal parameters 318 describe a movement and/or deflection 388 of the basilar membrane. Thus, the signal parameters 318 may, for example, describe a strength of the excitation of the basilar membrane for different locations along the basilar membrane. The deflection may here directly be described as a function of a position coordinate or in a different linearly or non-linearly transformed way. The signal parameters may thus describe the excitation of the basilar membrane as a function of place and time.

In a further embodiment, the signal parameters 318 describe the deflections 392 of several stereocilia which are arranged at different positions of the basilar membrane. Again, the signal parameters may describe the deflection of the stereocilia directly or in a transformed way.

In a similar way it is advantageous if the signal parameters 318 describe the calcium concentration 396, the transmitter release rate 400 or the neurotransmitter vesicle occurrence 404.

In a further embodiment it is advantageous that the signal parameters 318 directly describe the neural activity pattern 408 which characterizes the excitation of several auditory nerves. In this case, the signal parameters 318 give direct information about individual stimulation impulses which the cochlear implant 342 has to provide for an excitation of nerve cells.

Depending on which of the mentioned internal state variables of the simulation model 370 are used as signal parameters 318, it is the task of the cochlear implant 342 to generate the nerve cell stimulation signals suitable for the cochlear implant from the internal state variable of the hearing model 370 described by the signal parameters 318. It has turned out to be especially advantageous not to transmit the neural activity pattern 408 and/or nerve cell stimulation signals directly as signal parameters, but advantageously parameters which describe a movement 388 of the basilar membrane or a deflection 392 of the stereocilia, as in this case the nerve cell stimulation signals may be derived from the signal parameters with less computing overhead for cochlear implants with different electrode arrangements. Thus, a description of the basilar membrane movement 388 or an excitation 392 of the hair cells enables a modeling independent of the cochlear implant which is suitable for standardization, wherein the individual cochlear implant 342 only has to perform a comparatively small part of the overall computing overhead for the calculation of the nerve cell stimulation signals.

It is further to be noted that the signal analysis 314 may further include a preprocessing of the audio signal 310. Thus, the audio signal and/or sound signal 310 may be optimized for controlling the cochlear implant 342 already before the actual application of the simulation model which describes human hearing, both in connection with a broadcast transmission 328 and in connection with a storage 364 of the encoded signal parameters 324.

For example, in the processing of a radio play within the scope of the signal analysis 314 background noise or background music may be omitted in order not to unnecessarily affect speech intelligibility. For this purpose, the signal analysis means 314 may, for example, include filters which underline a speech signal contained in the audio signal 310 and attenuate non-speech signals.

Further, the signal analysis means 314 may include a selection means for selecting individual channels of the audio signal 310 when the audio signal 310 is present in the form of a multi-channel signal. In this connection, from the overall audio signal 310, similar to a mixing desk, only those audio signal channels may be selected which are relevant for a wearer (carrier) of the cochlear implant 342. Thus, the inventive concept enables, within the scope of preprocessing of the audio signal 310, to provide optimized information about the audio signal 310 in the form of audio signal parameters 342 for a wearer of the cochlear implant 342.

Figure 4:
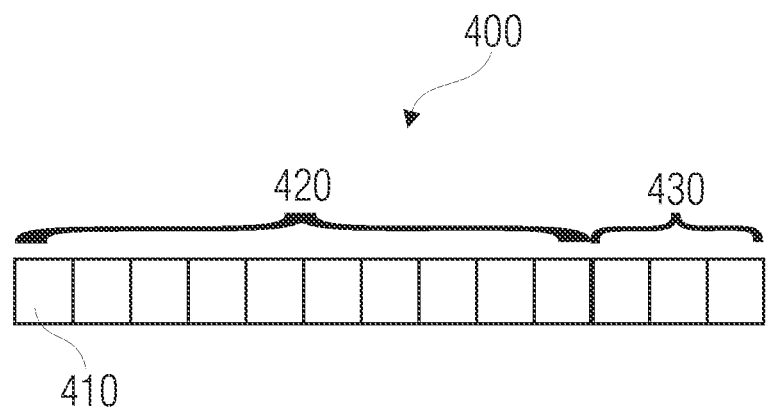
FIG. 4 shows a schematical illustration of an inventive combination signal according to a fifth embodiment of the present invention.

FIG. 4 shows a schematical illustration of an inventive combination signal according to a fifth embodiment of the present invention. The graphical illustration of FIG. 4 is designated by 400 in its entirety. An inventive combination signal is here symbolically illustrated by a plurality of bits 410. A first portion 420 of the combination signal 400 for example describes an audio signal for a reproduction for a person with a healthy hearing system in an encoded or non-encoded form. A second portion 430 of the combination signal, however, describes signal parameters in an encoded or non-encoded form which are suitable and/or adapted for controlling a cochlear implant to generate a representation of the audio signal described by the first portion 420 of the combination signal 400 by the cochlear implant. The signal parameters contained in the second portion 430 of the combination signal 400 may, for example, describe a basilar membrane movement and/or basilar membrane deflection 388 which results when the human hearing simulation model 370 is pulsed with the audio signal. In a similar way, the second portion 430 of the combination signal may describe an excitation of hair cells in a hearing model (for example in the hearing model 370). Likewise, the second portion 430 of the combination signal 400 may, for example, describe stimulation impulses which give a hearing impression with a corresponding stimulation of auditory nerves of a patient which corresponds to the underlying audio signal.

It is to be noted here that both the first portion 420 and also the second portion 430 of the inventive combination signal may be encoded in any way. For example, the first portion 420 of the combination signal 400 and/or the second portion 430 of the combination signal 400 may comprise source encoding or channel encoding. Apart from that, it is also possible that the first portion 420 and the second portion 430 of the combination signal 400 comprise a common source encoding or a common channel encoding. The first portion 420 of the combination signal and the second portion 430 of the combination signal 400 may, for example, be transmitted in a time-coordinated way in different channels of a transmission means. The two portions, 420, 430 of the combination signal 400 may further also be separated onto different carriers or sub-carriers of the same telecommunication channel. Further, the first portion 420 and the second portion 430 of the combination signal may be transmitted in a time-coordinated way in a time division multiplex or a frequency division multiplex. Individual bits of the first portion 420 and the second portion 430 may further be interleaved. A substantial feature of the inventive combination signal 400 is, however, a time-coordinated transmission of the first portion 420 and the second portion 430 of the combination signal, wherein different modulation types and bit divisions may be used.

Apart from that, it is to be noted that the inventive combination signal 400 may also be stored on any data carrier.

Figure 5:
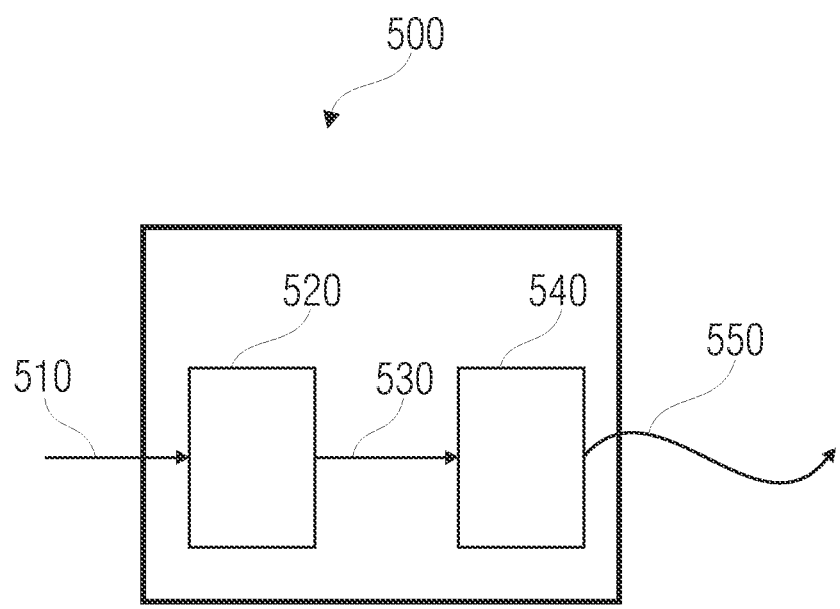
FIG. 5 shows a block diagram of an inventive means for generating a control signal for a cochlear implant according to a sixth embodiment of the present invention.

FIG. 5 shows a block diagram of an inventive device for generating a control signal for a cochlear implant according to a sixth embodiment of the present invention. The block diagram of FIG. 5 is designated by 500 in its entirety. The inventive device 500 is implemented to receive an audio signal 510. The audio signal 510 is supplied to a cochlear parameter extractor 520 which is implemented to analyze the audio signal to generate, based on an analysis of the audio signal, signal parameters 530 as input information for the cochlear implant. The cochlear parameter extractor 520 is implemented to perform the analysis of the audio signal 510 using a human hearing simulation model. The signal parameters 530 are here intermediate results or final results in the application of the simulation model. As a simulation model, for example the simulation model 370 illustrated in FIG. 3b may be chosen, wherein the cochlea parameter extractor 520 is implemented to process at least a part of the simulation model 370 and/or to determine at least an intermediate result 384, 388, 392, 396, 400, 404, 408 illustrated in a simulation model 370 and describe the same by the signal parameters 530.

In other words, due to the suitable implementation of the cochlear parameter extractor, the signal parameters 530 for example describe an oscillation excitation 384 of the cochlea, a basilar membrane movement 388, a deflection 392 of a stereocilium, a calcium concentration 396, a transmitter release rate 400, a neurotransmitter vesicle occurrence 404 or a neural activity pattern 408.

The device 500 further includes a transmit interface 540 for transmitting the signal parameters 530 to the cochlear implant. The transmit interface may be implemented wirelessly or by wire bonding and for example include an antenna, a line driver or a transmit induction loop.

It is further to be noted that the device 500 is implemented to be arranged and/or operated outside an ear into which the cochlear implant is introduced. This is advantageous as the device 500 typically comprises a high computing power and is implemented to provide more than 50% of the computing power necessary for the calculation of the nerve cell stimulation signals based on the audio signal. Thus, the cochlear implant only has to comprise a lower computing power than the device 500. By this division of tasks it may be guaranteed that the cochlear implant only has a low power consumption and is thus sufficiently small for an implantation into the human body. The device 500 may thus, in contrast to the cochlear implant, which is implemented to be firmly connected to the human body, advantageously be separated from the human body.

While the cochlear implant is, for example, implemented such that it may be introduced completely into an outer ear or an auditory channel of the human ear including the middle ear and the inner ear, the device 500 is implemented to be separable from the human body without a biological intervention.

Apart from that, it is advantageous that the device 500 is implemented as a telephone and/or a part of a telephone. In other words, the present invention further includes a telephone which comprises a device 500. In this case, the inventive device 500 receives a telephone audio signal as an audio signal 510 which would be supplied to a loudspeaker and/or a receiver inset in a conventional telephone. Further, the transmit interface 540 in the mentioned application is implemented to control an induction loop in order to transmit the signal parameters 530 to a cochlear implant. It has been shown that the integration of an inventive device 500 into a telephone brings substantial advantages as, by the inventive analysis of the audio signal 510 based on a human hearing simulation model, speech intelligibility may be substantially improved when speaking on the phone. As conventionally a telephone signal already comprises a comparatively low quality per se, it is extremely difficult for a patient with a cochlear implant, in connection with a conventional telephone and a conventional cochlear implant, to understand a message transmitted by phone. In contrast to that, by an inventive integration of the cochlear parameter extractor 520 into a telephone the transmission quality of the telephone can be considered in a provision of the signal parameters 530. Apart from that, an inventive combination offers substantial advantages regarding user comfort for the user and/or wearer of the cochlear implant.

The present invention further includes a plurality of methods which realize the inventive concept to supply signal parameters to a cochlear implant which are adapted for controlling the cochlear implant.

Figure 6A:
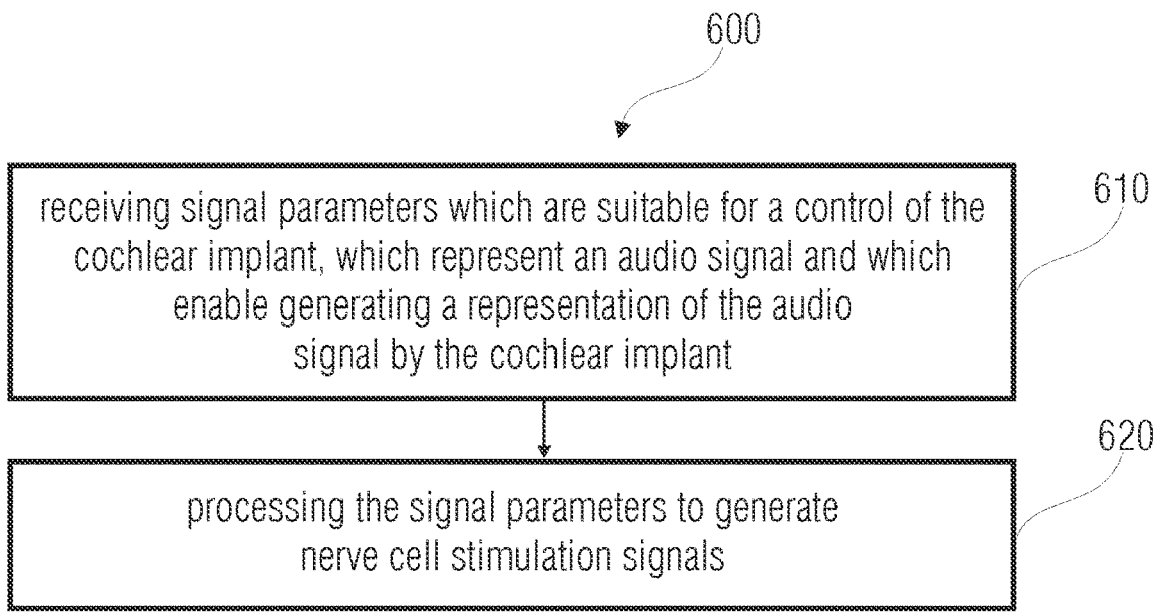
FIG. 6a shows a flowchart of an inventive method for operating a cochlear implant according to a seventh embodiment of the present invention.

FIG. 6a shows a flowchart of an inventive method for operating a cochlear implant according to a seventh embodiment of the present invention. It is assumed here that the cochlear implant is implemented in an inventive way in order to process signal parameters which are adapted for controlling the cochlear implant, which are based on an audio signal and which enable to generate a representation of the audio signal by the cochlear implant. The inventive method according to the seventh embodiment of the present invention is designated by 600 in its entirety. The method 600 includes a first step 610 of receiving signal parameters which are suitable for controlling the cochlear implant, which represent an audio signal and which enable generating a representation of the audio signal by the cochlear implant. The inventive method 600 further includes a second step 620 of processing the signal parameters to generate nerve cell stimulation signals.

Figure 6B:
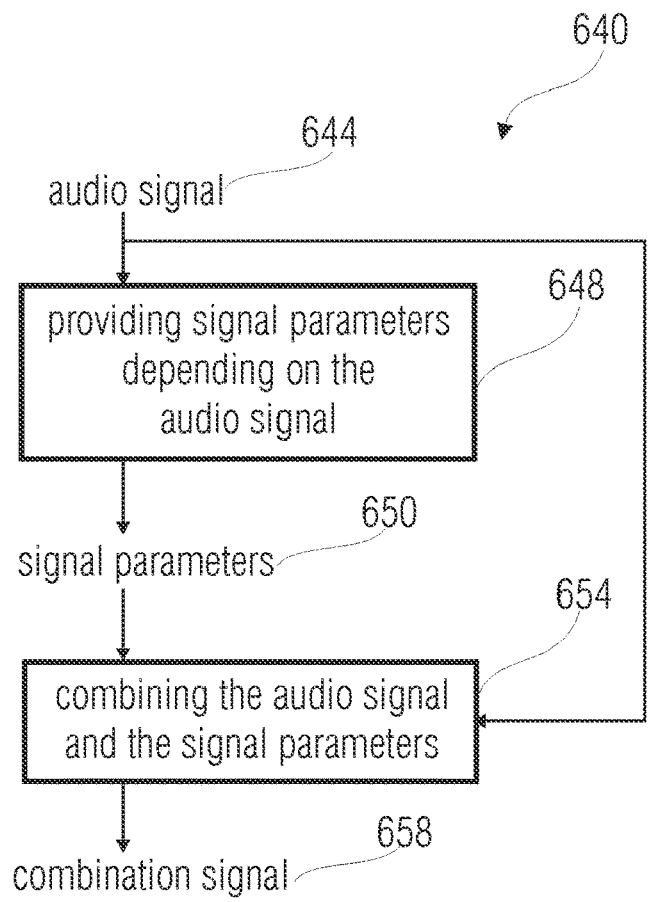
FIG. 6b shows a flowchart of an inventive method for generating a combination signal according to an eighth embodiment of the present invention.

FIG. 6b shows a flowchart of an inventive method for generating a combination signal according to an eighth embodiment of the present invention. The method illustrated in FIG. 6b is designated by 640 in its entirety. The inventive method 640 receives an audio signal 644 as an input variable. The method 640 includes a first step 648 of providing signal parameters 650 depending on the audio signal, as it was already described in detail above. A second step 654 further includes combining the audio signal 644 and the associated signal parameters 650, whereby a combination signal 658 is obtained.

Figure 6C:
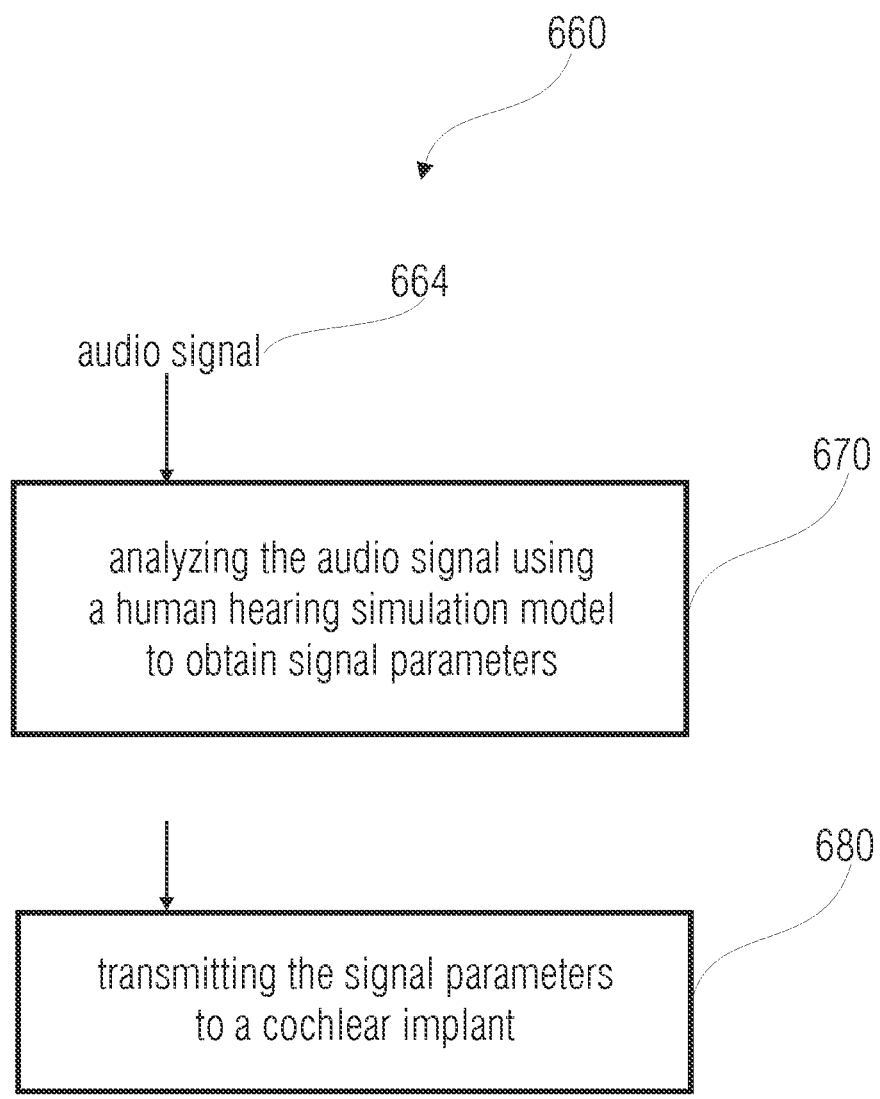
FIG. 6c shows a flowchart of an inventive method for generating a control signal for a cochlear implant according to a ninth embodiment of the present invention.
Figure 7A:
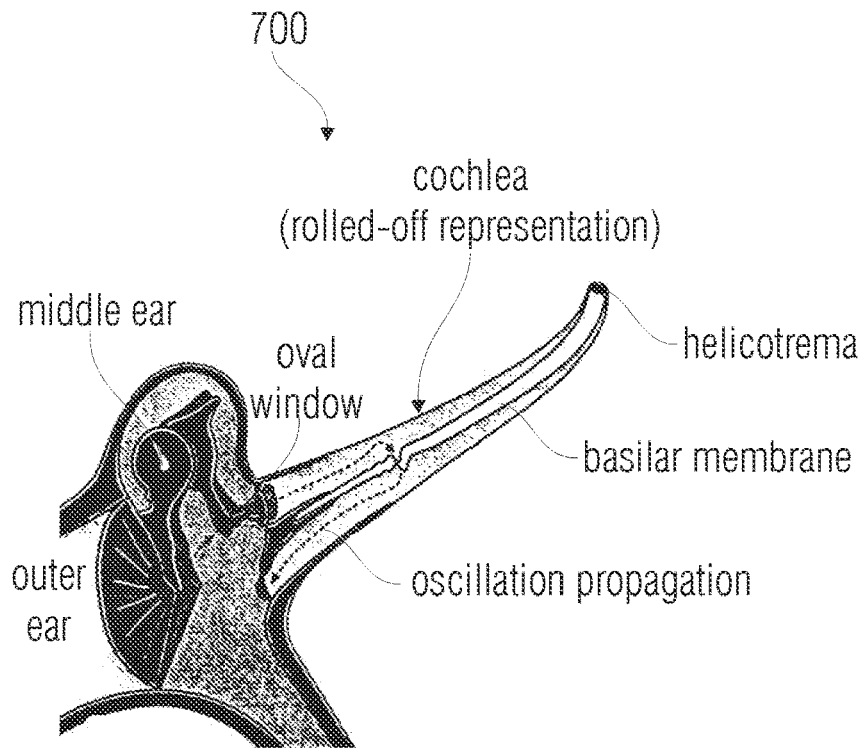
FIG. 7a shows a schematical illustration of a human ear.
Figure 7B:
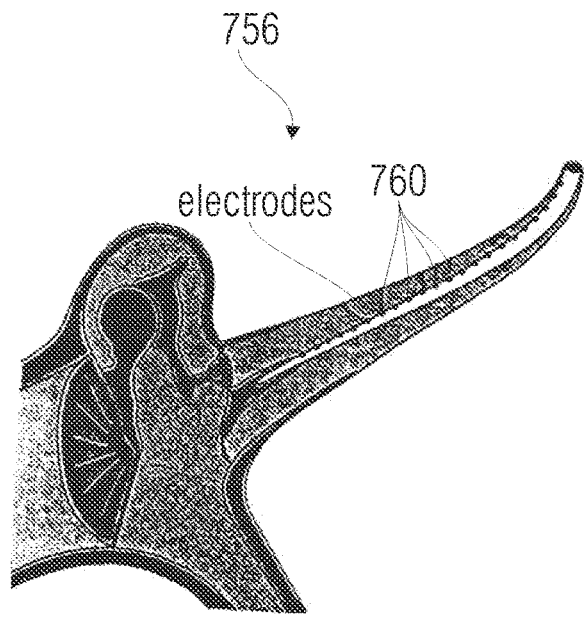
FIG. 7b shows a schematical illustration of a human ear into which electrodes of a cochlear implant are introduced.
Figure 8:
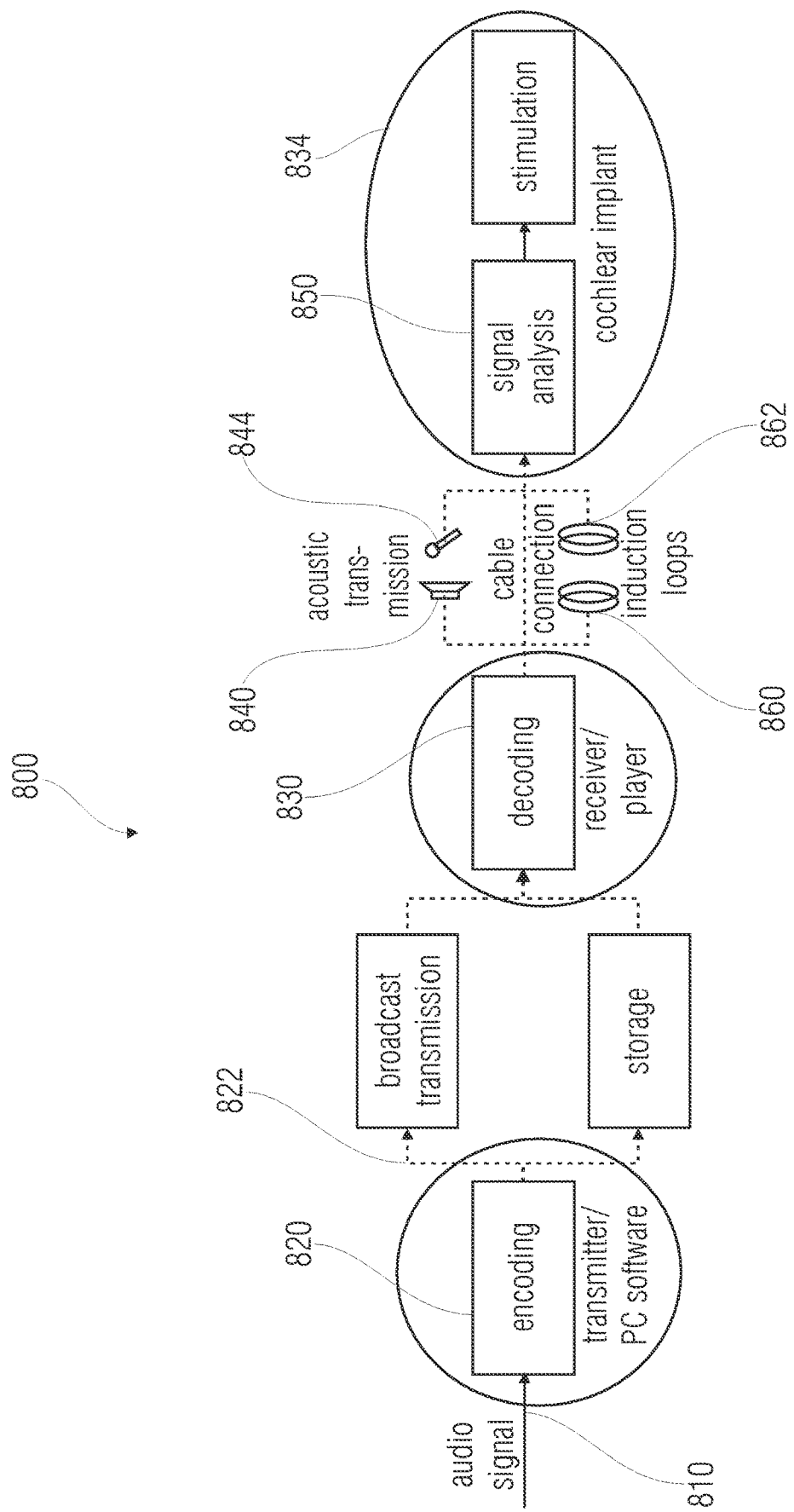
FIG. 8 shows a schematical illustration of conventional devices for coupling audio signals into a cochlear implant.

FIG. 6c further shows a flowchart of an inventive method for generating a control signal for a cochlear implant. The method illustrated in FIG. 6c is designated by 660 in its entirety. The method 660 receives an audio signal 664 as an input signal. A first step 670 includes analyzing the audio signal using a human hearing simulation model to obtain signal parameters belonging to the audio signal 664. A second step 680 further includes transmitting the obtained signal parameters to a cochlear implant.

It is to be noted here that the described methods 600, 640, 660 may be extended by all those features which were already described above with regard to the inventive devices.

Further, the inventive concept may be performed by a computer program. The inventive concept or method may, depending on the circumstances, be implemented in hardware or in software. The implementation may take place on a digital storage medium, for example a floppy disc, CD, DVD or a flash storage medium having electronically readable control signals which may cooperate with a programmable computer system so that the corresponding method is performed. In general, the invention thus also consists in a computer program product having a program code stored on a machine-readable carrier for performing the inventive method when the computer program product runs on a computer. In other words, the invention may thus be realized as a computer program having a program code for performing the method when the computer program runs on a computer.

In summary, it may thus be said that the present invention overcomes the disadvantages of conventional concepts for generating nerve cell stimulation signals in a cochlear implant. In conventional applications, for example in conventional radio or TV reception or in a reproduction of a sound signal by a portable media player, the audio signal and/or sound signal, which was actually produced for humans with a healthy hearing system, has to be converted in the signal processing unit of the cochlear implant (into nerve signals). Only when watching TV, additional subtitles may be used for improving the overall understanding.

It is thus the basic idea of the present invention that the largest part of signal processing in a transmission and/or storage of audio signals and/or sound signals does not have to take place in the signal processing unit of each individual cochlear implant but may be performed using more powerful processors. In a digital broadcast transmission, the corresponding signals processed on the transmitter side (also referred to as signal parameters) may then also be sent as side information. The signal processing units (of the cochlear implants) may then derive the stimulation impulses from the side information with a low computing overhead. Accordingly, also mobile players may be developed which store such preprocessed signals. Here, the conversion can take place when generating corresponding sound carriers, e.g. audio books, or at the home computer, in a similar way to the currently conventional encoding for MP3 players.

With a central signal processing in a broadcast transmitter or in a media production it may be considered that the generated side information be universally usable. That is, the side information should be in such a state that cochlear implants of different types may be controlled. Further, also an individual optimization of further processing should be possible for the individual carrier of a cochlear implant. Applications are also possible, however, in which an individual optimization of the signal processing is performed. For example, an individually configurable PC software may be implemented for writing to media for mobile players.

A modification of the above-described concept or method, respectively, may be used for improving speech quality when talking on the phone. Here a telephone apparatus developed especially for wearers of cochlear implants may take over the processing of the signal coming from a person talking. As far as a stationary device is used, the same may take over these complex signal processing steps, so that the signal processing unit of the cochlear implant, as described above, again only has to perform decoding and conversion. It thus turns out that the inventive concept may advantageously may be used in a telephone.

The present inventive concept thus enables a clear improvement of speech quality and/or speech intelligibility for patients with a cochlear implant. Further, the computing overhead needed within the cochlear implant may be clearly reduced so that a cochlear implant comprises a lower heat development and a lower current consumption.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. A device arranged to generate a combination signal based on an audio signal, comprising:
   a provider arranged to analyze the audio signal, to provide signal parameters based on the audio signal which are adapted to control a cochlear implant and which are implemented to generate a representation of the audio signal by the cochlear implant; and
   a signal combiner arranged to combine the audio signal and the signal parameters provided by the provider based on the audio signal to thereby obtain the combination signal in which the audio signal and the signal parameters are combined; wherein
   the combination signal comprises both the audio signal itself, which is for reproduction for a person with a healthy hearing system, and also the signal parameters, which are adapted to control the cochlear implant, such that the combination signal can be reproduced for persons with unimpaired hearing and also for persons with a cochlear implant.

2. The device according to claim 1, wherein the provider arranged to provide signal parameters depending on the audio signal includes a cochlear parameter extractor which is implemented to generate the signal parameters as input information for the cochlear implant based on an analysis of the audio signal.

3. The device according to claim 2, wherein the cochlear parameter extractor is implemented to calculate the signal parameters by inputting the audio signal into a human hearing simulation model, wherein the simulation model describes the analysis of the audio signal.

4. The device according to claim 2, wherein the device arranged to generate the combination signal is implemented to receive the audio signal in the form of several audio signal channels which comprise different audio signal contents, and wherein the device arranged to generate the combination signal further includes a channel selector which is implemented to select at least one audio signal channel of the audio signal for an analysis of the audio signal so that the analysis of the audio signal is only applied to a subset of the audio signal channels.

5. The device according to claim 2, wherein the device arranged to generate the combination signal is implemented to filter the audio signal to stress speech signals in the audio signal as compared to background noise in the audio signal to obtain a filtered audio signal and to use the filtered audio signal for the analysis.

6. The device according to claim 1, wherein the device arranged to generate the combination signal is implemented as a broadcast transmitter which is implemented to render the combination signal for an emission via an antenna.

7. The device according to claim 1, wherein the signal parameters describe a movement of a basilar membrane of a human ear based on the audio signal.

8. The device according to claim 1, wherein the signal parameters describe an excitation of hair cells in a human ear based on the audio signal.

9. The device according to claim 1, wherein the signal parameters describe stimulation impulses of auditory nerves of a human ear based on the audio signal.

10. The device according to claim 1, which is arranged to generate the combination signal so that a first part of the combination signal describes an audio signal for a reproduction for a person with a healthy hearing system, and so that a second part of the combination signal describes the signal parameters.

11. The device according to claim 1, wherein the device is arranged to encode the signal parameters and to associate a first group of sub-carriers with the audio signal for a broadcast transmission and associate a second group of sub-carriers with the encoded signal parameters.

12. The device according to claim 11, wherein the sub-carriers of the first group of sub-carriers and the sub-carriers of the second group of sub-carriers belong to the same main carrier.

13. A device arranged to generate a combination signal in which an audio signal and signal parameters are combined, the combination signal comprising the audio signal and the signal parameters which are adapted to control a cochlear implant and which are implemented to generate a representation of the audio signal by the cochlear implant; wherein
   the combination signal comprises both the audio signal itself, which is for reproduction for a person with a healthy hearing system, and also the signal parameters, which are provided based on an analysis of the audio signal and which are adapted to control the cochlear implant, such that the combination signal can be reproduced for persons with unimpaired hearing and also for persons with a cochlear implant.

14. The device according to claim 13, wherein the signal parameters are based on an analysis of the audio signal and describe input information for the cochlear implant.

15. The device according to claim 13, wherein the signal parameters describe a variable or an output variable of the simulation model occurring within a human hearing simulation model, wherein the variable represents the audio signal and results when the human hearing simulation model is excited by the audio signal as an input signal.

16. The device according to claim 13, wherein the signal parameters describe a movement of a basilar membrane of a human ear based on the audio signal.

17. The device according to claim 13, wherein the signal parameters describe an excitation of hair cells in a human ear based on the audio signal.

18. The device according to claim 13, wherein the signal parameters describe stimulation impulses of auditory nerves of a human ear based on the audio signal.

19. A method for generating a combination signal based on an audio signal, comprising:
  analyzing the audio signal, to provide signal parameters depending on the audio signal which are adapted to control a cochlear implant, which are based on the audio signal and which enable generating a representation of the audio signal by the cochlear implant; and
  combining the audio signal and the signal parameters which are provided based on the audio signal to obtain the combination signal in which the audio signal and the signal parameters are combined; wherein
  the combination signal comprises both the audio signal itself, which is for reproduction for a person with a healthy hearing system, and also the signal parameters, which are adapted to control the cochlear implant, such that the combination signal can be reproduced for persons with unimpaired hearing and also for persons with a cochlear implant.

20. A non-transitory computer-readable medium storing a computer program, when run on a computer, the computer program performs the method according to claim 19.

21. A device arranged to generate a combination signal based on an audio signal, comprising:
  a provider arranged to analyze the audio signal, to provide signal parameters depending on the audio signal which are adapted to control a cochlear implant and which are implemented to generate a representation of the audio signal by the cochlear implant; and
  a signal combiner arranged to combine the audio signal and the signal parameters provided by the provider to thereby obtain the combination signal in which the audio signal and the signal parameters are combined; wherein
  the combination signal comprises both the audio signal itself, which is for reproduction for a person with a healthy hearing system, and also the signal parameters, which are adapted to control the cochlear implant, such that the combination signal can be reproduced for persons with unimpaired hearing and also for persons with a cochlear implant; and
  the device arranged to generate the combination signal is implemented as a broadcast transmitter arranged to render the combination signal for an emission via an antenna.

22. A system, comprising:
  a device that generates and transmits a combination signal based on an audio signal, the device including:
    a provider that provides signal parameters based on the audio signal which are adapted to control a cochlear implant and which are implemented to generate a representation of the audio signal by the cochlear implant; and
    a signal combiner that combines the audio signal and the signal parameters provided by the provider based on the audio signal to thereby obtain the combination signal; wherein
    the combination signal includes both the audio signal itself, which is for reproduction for a person with a healthy hearing system, and also the signal parameters, which are adapted to control the cochlear implant, such that the combination signal can be reproduced for persons with unimpaired hearing and also for persons with a cochlear implant;
  a plurality of first cochlear implants that receive and process the signal parameters which are provided by the provider based on the audio signal and are adapted to control the plurality of first cochlear implants, each of the plurality of first cochlear implants using the signal parameters to generate a representation of the audio signal and including:
    a receive interface that receives the signal parameters; and
    a nerve stimulator that processes the signal parameters to generate nerve cell stimulation signals based on the signal parameters; and
  a second cochlear implant that processes the audio signal itself.

23. A device arranged to generate a combination signal based on an audio signal, comprising:
  a provider arranged to analyze the audio signal, to provide signal parameters based on the audio signal which are adapted to control a cochlear implant and which are implemented to generate a representation of the audio signal by the cochlear implant; and
  a signal combiner arranged to combine the audio signal and the signal parameters provided by the provider based on the audio signal to thereby obtain the combination signal in which the audio signal and the signal parameters are combined; wherein
  the combination signal comprises both the audio signal itself, which is for reproduction for a person with a healthy hearing system, and also the signal parameters, which are adapted to control the cochlear implant, such that the combination signal can be reproduced for persons with unimpaired hearing and also for persons with a cochlear implant;
  the provider arranged to provide signal parameters depending on the audio signal includes a cochlear parameter extractor which is implemented to generate the signal parameters as input information for the cochlear implant based on an analysis of the audio signal; and
  the cochlear parameter extractor is implemented to calculate the signal parameters by inputting the audio signal into a human hearing simulation model, wherein the simulation model describes the analysis of the audio signal.

* * * * *